US010798940B2

(12) United States Patent
Uhr et al.

(10) Patent No.: US 10,798,940 B2
(45) Date of Patent: Oct. 13, 2020

(54) PENFLUFEN POLYMER PARTICLES

(71) Applicant: LANXESS Deutschland GmbH, Cologne (DE)

(72) Inventors: Hermann Uhr, Leverkusen (DE); Thomas Jaetsch, Cologne (DE)

(73) Assignee: LANXESS Deutschland GmbH, Cologne (DE)

( * ) Notice: Subject to any disclaimer, the term of this patent is extended or adjusted under 35 U.S.C. 154(b) by 34 days.

(21) Appl. No.: 15/753,209

(22) PCT Filed: Aug. 10, 2016

(86) PCT No.: PCT/EP2016/069047
§ 371 (c)(1),
(2) Date: Feb. 16, 2018

(87) PCT Pub. No.: WO2017/036755
PCT Pub. Date: Mar. 9, 2017

(65) Prior Publication Data
US 2018/0235222 A1    Aug. 23, 2018

(30) Foreign Application Priority Data
Sep. 2, 2015 (EP) .................... 15183408

(51) Int. Cl.
| A01N 25/10 | (2006.01) |
| A01N 43/56 | (2006.01) |
| C07D 231/18 | (2006.01) |
| C08F 2/44 | (2006.01) |
| C08L 33/08 | (2006.01) |
| C08L 33/10 | (2006.01) |
| C08F 2/22 | (2006.01) |
| C08F 18/00 | (2006.01) |
| C08F 10/00 | (2006.01) |
| C08F 20/00 | (2006.01) |
| C08F 220/14 | (2006.01) |

(52) U.S. Cl.
CPC ............. *A01N 43/56* (2013.01); *A01N 25/10* (2013.01); *C07D 231/18* (2013.01); *C08F 2/22* (2013.01); *C08F 2/44* (2013.01); *C08F 10/00* (2013.01); *C08F 18/00* (2013.01); *C08F 20/00* (2013.01); *C08L 33/08* (2013.01); *C08L 33/10* (2013.01); *C08F 220/14* (2013.01)

(58) Field of Classification Search
CPC .... C08F 2/22; C08F 2/44; C08F 10/00; C08F 18/00; C08F 20/00; C08F 220/14; C08L 33/08; C08L 33/10; C07D 231/18; A01N 43/56; A01N 25/10
See application file for complete search history.

(56) References Cited

U.S. PATENT DOCUMENTS

| 5,990,221 A * | 11/1999 | Dames ...................... C08F 2/24 524/457 |
| 7,354,596 B1 * | 4/2008 | Banovetz ............... A01N 25/10 424/405 |
| 7,538,073 B2 | 5/2009 | Elbe et al. |
| 8,741,968 B2 | 1/2014 | Goettsche et al. |
| 9,596,854 B2 | 3/2017 | Koop et al. |
| 10,231,459 B2 | 3/2019 | Koop et al. |
| 2014/0079806 A1 * | 3/2014 | Koop ..................... A01N 43/56 424/635 |
| 2019/0150453 A1 | 5/2019 | Koop et al. |

OTHER PUBLICATIONS

International Search Report from corresponding International Application No. PCT/EP2016/069047, dated Nov. 3, 2016, two pages.

* cited by examiner

*Primary Examiner* — Irina S Zemel
*Assistant Examiner* — Jeffrey S Lenihan
(74) *Attorney, Agent, or Firm* — Nicanor A. Kohncke

(57) ABSTRACT

The invention relates to penflufen-containing polymer particles, to penflufen-containing compositions comprising them, to processes for preparing them, and to the use thereof for protecting technical materials, more particularly wood, wood products, and wood-plastic composites.

14 Claims, No Drawings

PENFLUFEN POLYMER PARTICLES

The invention relates to penflufen-containing polymer particles, to penflufen-containing compositions comprising them, to processes for preparing them, and to the use thereof for protecting technical materials, more particularly wood, wood products, and wood-plastic composites.

Penflufen (N-(2-[1,3-dimethylbuthylphenyl]-5-fluoro-1,3-dimethyl-1H-pyrazole-4-carboxamide, CAS No. 494793-67-8) is an active fungicidal ingredient from the class of the pyrazolylcarboxanilides of the formula (I) and is known from WO 20031010149 A1.

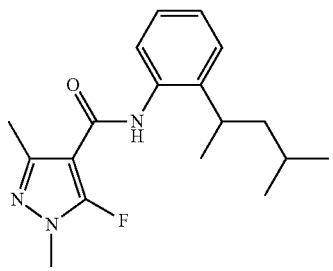

(I)

From WO 2012055673 A1 and from WO 2012055674 A1 it is known that penflufen can be utilized especially for controlling wood-destroying fungi.

Encapsulation of active fungicidal ingredients may be advisable for a variety of reasons. As well as the possibility of releasing active ingredients in a dosed manner and so extending the long-term protection afforded by the fungicides, another possible reason is the reduction in organic solvents or emulsifiers, as is known from EP 1742531 B1.

EP 1742531 B1 describes a process for preparing encapsulated, water-insoluble fungicides, in which the fungicides are dissolved in the monomers and then the monomers are polymerized by way of a conventional radical emulsion polymerization. In the case of the conventional emulsion polymerization, water, monomer or monomer mixtures, optionally surfactants, protective colloids, and a water-soluble initiator are emulsified and this emulsion is polymerized. This polymerization takes place in the water phase or in micelles of the surfactant. The monomer is supplied continuously from the oil droplets for the polymerization, via the water phase. A disadvantage of the process known from EP 1742531 B1 is that it cannot be used to encapsulate penflufen, since too great a quantity of crystallized penflufen or of penflufen adhered to the polymer is formed.

There continues, consequently, to be demand for stable, penflufen-containing polymer particles.

Surprisingly it has now been found that stable, penflufen-containing polymer particles can be prepared if oil-soluble radical initiators are used in the emulsion polymerization.

A subject of the invention are therefore penflufen-containing polymer particles prepared by polymerization of at least one ethylenically unsaturated monomer in the presence of penflufen or its salts and acid addition compounds and in the presence of an oil-soluble radical initiator, optionally in the presence of further auxiliaries, in an oil-in-water emulsion polymerization.

Whenever the present specification refers to penflufen-containing polymer particles, these are polymer particles comprising penflufen or its salts and acid addition compounds.

For the purposes of the invention, penflufen may be used alternatively as the racemate, in an enantiomerically pure form, or as enriched enantiomer mixture. Also possible is use in the form of a salt or acid addition compound, in which case salts include, in particular, sodium, potassium, magnesium, calcium, zinc, aluminum, iron, and copper, and acid addition compounds include, in particular, adducts with hydrohalic acids, e.g., hydrogen chloride and hydrogen bromide, carboxylic acids, such as formic acid, acetic acid, tartaric acid, and oxalic acid, sulfonic acids, such as p-toluenesulfonic acid, and also sulfuric acid, phosphoric acid, and nitric acid. Preference is given to using penflufen.

The ethylenically unsaturated monomers may either be pure substances or else mixtures of two or more ethylenically unsaturated monomers.

The monomers are preferably neutral, uncharged, ethylenically unsaturated monomers, which are given the designation M1.

Suitable monomers M1 preferably comprise vinylaromatic monomers such as styrene, divinylbenzene, esters of monoethylenically unsaturated monocarboxylic and dicarboxylic acids having 3 to 8 and more particular 3 or 4 carbon atoms with $C_1$-$C_{20}$ alkanols or with $C_5$-$C_8$ cycloalkanols, more particularly the esters of acrylic acid, of methacrylic acid, of crotonic acid, the diesters of maleic acid, of fumaric acid and of itaconic acid, and more preferably the esters of acrylic acid with $C_1$-$C_{18}$ alkanols (=$C_1$-$C_{18}$ alkyl acrylates) such as methyl acrylate, ethyl acrylate, n-butyl acrylate, isobutyl acrylate, tert-butyl acrylate, n-hexyl acrylate, 2-ethylhexyl acrylate, 3-propylheptyl acrylate and stearyl acrylate, and also the esters of methacrylic acid with $C_1$-$C_{18}$ alkanols such as methyl methacrylate, ethyl methacrylate, n-butyl methacrylate, isobutyl methacrylate, tert-butyl methacrylate, n-hexyl methacrylate and stearyl methacrylate. Further suitable monomers M1 are vinyl and allyl esters of aliphatic carboxylic acids having 1 to 20 carbon atoms, examples being vinyl acetate, vinyl propionate, and the vinyl esters of Versatic® acids (vinyl versatates), vinyl halides such as vinyl chloride and vinylidene chloride, conjugated diolefins such as butadiene and isoprene, and also $C_2$-$C_6$ olefins, such as ethylene, propene, 1-butene and n-hexene. Preferred monomers are vinylaromatic monomers, especially styrene, divinylbenzene, $C_1$-$C_{20}$ alkyl acrylates, especially $C_1$-$C_{18}$ alkyl acrylates and $C_1$-$C_{18}$ alkyl methacrylates.

Additionally suitable as monomers M1 are also amides of the aforesaid ethylenically unsaturated carboxylic acids, especially acrylamide and methacrylamide, ethylenically unsaturated nitriles such as methacrylonitrile and acrylonitrile, hydroxyalkyl esters of the aforesaid α,β-ethylenically unsaturated $C_3$-$C_8$ monocarboxylic acids and of the $C_4$-$C_8$ dicarboxylic acids, especially hydroxyethyl acrylate, hydroxyethyl methacrylate, 2 and 3 hydroxypropyl acrylate, 2- and 3-hydroxypropyl methacrylate, esters of the aforesaid monoethylenically unsaturated monocarboxylic and dicarboxylic acids with $C_2$-$C_4$ polyalkylene glycols, especially the esters of these carboxylic acids with polyethylene glycol or alkyl polyethylene glycols, with the (alkyl)polyethylene glycol radical customarily having a molecular weight in the range from 100 to 3000 g/mol.

Further monomers M1 are N-vinyl amides such as N-vinylformamide, N-vinylpyrrolidone, N-vinylimidazole and N-vinylcaprolactam.

In general the polymer is composed of at least 60 wt % of monomers M1, based on the total amount of monomers used. The fraction of monomers M1 is preferably at least 70 wt %, more preferably at least 80 wt %.

In addition to the monomers M1, it is also possible, optionally, for ethylenically unsaturated monomers having anionic or cationic groups to be copolymerized, these being charged ethylenically unsaturated monomers. The ethylenically unsaturated monomers having anionic or cationic groups receive the designation M2.

The monomers M2 include, in particular, monoethylenically unsaturated monomers which have at least one anionic group, more particularly monomers which have at least one acid group, preferably at least one sulfonic acid group, one phosphonic acid group, or one or two carboxylic acid groups, and also the salts of the monomers, especially the alkali metal salts, examples being the sodium or potassium salts, and also the ammonium salt; furthermore, ethylenically unsaturated sulfonic acids, especially vinyl sulfonic acid, 2-acrylamido-2-methylpropane sulfonic acid, 2-acryloyloxyethanesulfonic acid and 2-methacryloyloxyethanesulfonic acid, 3-acryloyloxy- and 3-methacryloyloxypropanesulfonic acid, vinylbenzene sulfonic acid and salts thereof, ethylenically unsaturated phosphonic acids such as vinylphosphonic acid and dimethyl vinylphosphonate and salts thereof, and α,β-ethylenically unsaturated $C_3$-$C_8$ monocarboxylic and $C_4$-$C_8$ dicarboxylic acids, especially acrylic acid, methacrylic acid, crotonic acid, maleic acid, fumaric acid and itaconic acid. Preferred for use as monomers M2 are α,β-ethylenically unsaturated $C_3$-$C_8$ monocarboxylic and C4-C8 dicarboxylic acids.

The monomers M2 may further include, in particular, monoethylenically unsaturated monomers which have at least one cationic group and/or at least one group which can be protonated in an aqueous environment. The cationic monomers M2 include, in particular, those which have a protonatable amino group, a quaternary ammonium group, a protonatable imino group or a quaternized imino group. Examples of monomers M2 having a protonatable imino group are N-vinylimidazole and vinylpyridines. Examples of monomers M2 having a quaternized imino group are N-alkylvinylpyridinium salts and N-alkyl-N'-vinylimidazolinium salts such as N-methyl-N'-vinylimidazolinium chloride or methosulfate.

Examples of monomers M2 having protonatable amino groups are, for example and preferably, 2-(N,N-dimethylamino)ethyl acrylate, 2-(N,N-dimethylamino)ethyl methacrylate, 2-(N,N-dimethylamino)ethylacrylamide, 3-(N,N-dimethylamino)propylacrylamide, 3-(N,N-dimethylamino)propylmethacrylamide, 2-(N,N-dimethylamino)ethylmethacrylamide, and they may take the form, for example, of $Cl^-$, $HSO^{4-}$, ½ $SO_4^{2-}$ or $CH_3OSO_3^-$ salts. Monomers having quaternary ammonium compounds are, for example and preferably, 2-(N,N,N-trimethylammonium)ethyl acrylate chloride, 2-(N,N,N-trimethylammonium)ethyl methacrylate chloride, 2-(N,N,N-trimethylammonium)ethylmethacrylamide chloride, 3-(N,N,N-trimethylammonium)propylacrylamide chloride, 3-(N,N,N-trimethylammonium)propylmethacrylamide chloride, 2-(N,N,N-trimethylammonium)ethylacrylamide chloride, and also the corresponding methosulfates and sulfates.

The fraction of the monomers M2 is preferably not greater than 35 wt %, more preferably not greater than 20 wt %, based on the total amount of monomers used. Very particular preference is given to using 80 wt % to 99.9 wt % of monomers M1 and 0.1 wt % to 20 wt % of monomers M2, based on the total amount of monomers used.

In a further preferred embodiment, the amount of charged monomers M2 in the polymer is less than 0.01 wt %, based on the total amount of monomers used.

As radical, oil-soluble initiator it is possible to use oil-soluble per, oxo and azo compounds, which may be employed individually or else as mixtures. These include azo compounds, such as 2,2'-azobisisobutyronitrile, 2,2'-azobis(2-methylbutyronitrile), 2,2'-azobis[2-methyl-N-(2-hydroxyethyl)propionamide, 1,1'-azobis(1-cyclohexanecarbonitrile), 2,2°-azobis[2,4-dimethylvaleronitrile), 2,2'-azobis(N,N'-dimethyleneisobutyroamidine) dihydrochloride, and 2,2'-azobis(2-amidinopropane) dihydrochloride, organic or inorganic peroxides such as diacetyl peroxide, di-tert-butyl peroxide, diamyl peroxide, dioctanoyl peroxide, didecanoyl peroxide, dilauroyl peroxide, dibenzoyl peroxide, bis(o-toluoyl) peroxide, succinyl peroxide, tert-butyl peracetate, tert-butyl permaleinate, tert-butyl perisobutyrate, tert-butyl perpivalate, tert-butyl peroctoate, tert-butyl perneodecanoate, tert-butyl perbenzoate, tert-butyl peroxide, tert-butyl hydroperoxide, cumene hydroperoxide, tert-butyl peroxi-2-ethylhexanoate and diisopropyl peroxidicarbamate.

Very preferably the radical initiators are 2,2'-azobisisobutyronitrile, 2,2'-azobis(2-methylbutyronitrile) or mixtures of these initiators. The radical initiators are used in general in an amount of 0.1 wt % to 5 wt %, based on the total amount of monomers. The radical initiator is used preferably in an amount of 0.1 wt % to 3 wt %, based on the total amount of monomers.

It is possible optionally, moreover, to use further auxiliaries such as, for example, costabilizers, surface-active substances, such as protective colloids and low molecular weight emulsifiers, for example, solvents and plasticizers. If auxillaries are used, they are preferably costabilizers, emulsifiers and solvents.

The costabilizers optionally employed are substances which stabilize the microemulsion with respect to Ostwald ripening and which have a very low solubility in the continuous phase. They are preferably long-chain, linear, cyclic or branched aliphatic hydrocarbons selected from the group consisting of $C_{14}$-$C_{25}$ alkanes and $C_{14}$-$C_{25}$ cycloalkanes. More preferably they are $C_{14}$-$C_{18}$ alkanes and $C_{14}$-$C_{18}$ cycloalkanes, and especially preferably are tetradecane, pentadecane, hexadecane, heptadecane, octadecane and nonadecane or mixtures of these costabilizers.

If costabilizers are used, the amount is in general between 0.05 to 20 wt %, preferably between 0.1 to 15 wt % and very preferably between 0.2 and 10 wt %, based on the total amount of monomers used.

As solvents and plasticizers it is possible in general to use all substances which behave inertly toward the monomers, the resultant polymer, and the penflufen.

Preferred solvents used are inert, dipolar, aprotic, organic solvents, such as, in particular, esters of dihydric carboxylic acids—for example and preferably, mixtures comprising diisobutyl adipate, diisobutyl glutarate, diisobutyl succinate (e.g., Rhodiasolv DIB), and also benzyl alcohol, polyethylene glycols and polypropylene glycols.

Plasticizers used are preferably phthalates, such as, in particular, diethylhexyl phthalate (DEHP), dibutyl phthalate (BBP), diisononyl phthalate (DINP), diisodecyl phthalate (DIDP), diisooctyl phthalate (DNOP), diisobutyl phthalate (DIBP), diisohexyl phthalate, diisoheptyl phthalate, di-n-octyl phthalate, diisoundecyl phthalate, diisotredecyl phthalates; adipates, such as, in particular, diethylhexyl adipate (DEHA), diisooctyl adipate, diisononyl adipate, polyesters of adipic acid or glutaric acid, such as, in particular, Ultramoll IV® from Lanxess Deutschland GmbH; trialkyl esters of citric acid or acetylated trialkyl esters of citric acid, such as, in particular, acetyl tributyl citrate (ATBC); esters of trimellitic acid, such as, in particular, tri(2-ethylhexyl) trimellitate, tri(isooctyl) trimellitate, tri(isononyl) trimellitate; 1,2-dicyclohexyl-based plasticizers, such as, in particular, 1,2-cyclohexanedicarboxylic acid nonyl ester (Hexamoll®, DINCH); alkylsulfonic esters of phenol, such as, in particular, Mesamoll® from Lanxess Deutschland GmbH (CAS-No. 091082-17-6); acetylated mono- and diglycerides; benzoic diesters, such as, in particular, dialkylene glycols, such as, in particular, dipropylene glycol dibenzoate or isononyl benzoate; trimethylolpropane esters such as, in particular, trimethylolpropane benzoate/2-ethylhexanoate mixtures; dialkyl esters of terephthalic acid, such as, in particular, di-2-ethythexyl terephthalate.

Surface-active substances include not only protective colloids but also low molecular weight emulsifiers, the latter differing from the protective colloids and having preferably a molecular weight between 2000 g/mol, more particularly below 1000 g/mol (mass average). The protective colloids and low molecular weight emulsifiers may be either cationic, anionic, neutral or else zwitterionic in nature.

Examples of anionic surface-active substances are anionic emulsifiers of low molecular weight, such as, for example and preferably, alkylphenylsulfonates, phenylsulfonates, alkyl sulfates, alkylsulfonates, alkyl ether sulfates, alkylphenol ether sulfates, alkylpolyglycol ether phosphates, alkyldiphenyl ether sulfonates, polyarylphenyl ether phosphates, alkylsulfosuccinates, olefinsulfonates, paraffinsulfonates, petroleumsulfonates, taurides, sarcosides, fatty acids, alkylnaphthalenesulfonic acids, naphthalenesulfonic acids, including the alkali metal, alkaline earth metal, ammonium and amine salts thereof.

Anionic protective colloids are, for example and preferably, lignosulfonic acids, condensation products of sulfonated naphthalenes with formaldehyde or with formaldehyde and phenol and optionally urea, and also condensation products of phenolsulfonic acid, formaldehyde and urea, lignin-sulfite waste liquor and lignosulfonates, and also polycarboxylates such as polyacrylates, maleic anhydride/olefin copolymers, and also the alkali metal, alkaline earth metal, ammonium and amine salts of the aforesaid protective colloids. Nonionic protective colloids are, for example and preferably, polyethylene glycol, polypropylene glycol, polyethylene glycol-polypropylene glycol block copolymers, polyethylene glycol alkyl ethers, polypropylene glycol alkyl ethers, polyethylene glycol polypropylene glycol ether block copolymers, and mixtures thereof.

Further protective colloids of high molecular weight are, for example and preferably, carboxymethylcellulose, natural and synthetic pulverulent, granular or latex-like polymers, such as gum arabic, polyvinyl alcohol, polyvinyl acetate, and natural phospholipids, such as cephalins and lecithins and synthetic phospholipid and also liquid paraffins.

Nonionic emulsifiers of low molecular weight are, for example and preferably, alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone fluids, alkylpolyglycosides and glycerol-fatty acid esters.

Cationic emulsifiers of low molecular weight are, for example and preferably, quaternary ammonium salts, e.g., trimethyl- and triethyl-$C_6$-$C_{30}$ alkylammonium salts, such as cocotrimethylammonium salts, trimethylcetylammonium salts, dimethyl- and diethyl-di-$C_4$-$C_{20}$ alkylammonium salts, such as didecyldimethylammonium salts and dicocodimethylammonium salts, methyl- and ethyl-tri-$C_4$-$C_{20}$ alkylammonium salts, such as methyltrioctylammonium salts, $C_1$-$C_{20}$ alkyl-di-C1-C4-alkylbenzylammonium salts, such as triethylbenzylammonium salts and cocobenzyldimethylammonium salts, methyl- and ethyl-di-$C_4$-$C_{20}$ alkylpoly(oxyethyl)ammonium salts, e.g., didecylmethylpoly(oxyethyl) ammonium salts, N-$C_6$-$C_{20}$ alkylpyridiriium salts, e.g., N-laurylpyridinium salts, N-methyl- and N-ethyl-N-$C_6$-$C_{20}$ alkylmorpholinium salts, and also N-methyl- and N-ethyl-N'-$C_6$-$C_{20}$ alkylimidazolinium salts, especially the halides, borates, carbonates, formates, acetates, propionates, hydrogen carbonates, sulfates and methosulfates.

Zwitterionic emulsifiers of low molecular weight are those having betaine structures. Substances of this kind are known to the skilled person and can be found in the relevant prior art (see, for example, R. Heusch, in Ullmann's Encyclopedia of Industrial Chemistry, 5th. ed, on CD-ROM, Wiley-VCH 1997, "Emulsions", chapter 7, table 4).

The amount of low molecular weight emulsifier is customarily in the range from 0.1 wt % to 15 wt %, more particularly in the range from 0.2 wt % to 12 wt % and more preferably 0.7 wt % to 10 wt %, based on the total amount of monomers used.

In order to increase the activity but also in order to preserve the resultant suspensions, the penflufen-containing polymer particles may optionally comprise further antimicrobially active compounds, fungicides, bactericides, herbicides, insecticides or other active ingredients. These mixtures may possess an even broader activity spectrum. These compounds, like the penflufen, are used in dispersion or solution in the monomers. In many cases, the effects obtained here are synergistic, meaning that the activity of the mixture is greater than the activity of the individual components. Examples of particularly useful co-components are the following compounds:

triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeoconazole, (+)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl)-propan-2-ol, tebuconazole tetraconazole, triadimefon, triadimenol, triapenthenol, triflumizole, triticonazole, uniconazole, and their metal salts and acid adducts;

imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar 1-imidazolyl-1-(4'-chlorophenoxy)-3,3-dimethylbuton-2-one, and metal salts and acid adducts thereof;

pyridines and pyrimidines such as:
ancymidol, buthiobat, fenarimol, mepanipyrin, nuarimol, pyroxyfur, triamirol;

succinate dehydrogenase inhibitors such as:
benodanil, carboxim, carboxim sulfoxide, cyclafluramid, fenfuram, flutanil, furcarbanil, furmecyclox, mebenil, mepronil, methfuroxam, metsulfovax, nicobifen, pyrocarbolid, oxycarboxin, shirlan, seedvax;

naphthalene derivatives such as:
terbinafin, naftilin, butonalin, 3-chloro-7-(2-aza-2,7,7-trimethyl-oct-3-en-5-yne);

sulfenamides such as:

dichlofluanid, tolylfluanid folpet, fluorfolpet; captan, captofol;

benzimidazoles such as:

carbendazim, benomyl, fuberidazole, thiabendazolo or salts thereof;

morpholine derivatives such as:

aldimorph, dimethomorph, dodemorph, falimorph, fenpropidin fenpropimorph, tridemorph, trimorphamid and their arylsulfonic acid salts, such as e.g. p-toluenesulfonic acid and p-dodecylphenylsulfonic acid;

benzothiazoles such as:

2-mercaptobenzothiazole;

benzthiophene dioxides such as:

benzo[b]thiophene S,S-dioxide-carboxylic acid cyclohexylamide;

benzamides such as:

2,6-dichloro-N-(4-trifluoromethylbenzyl)benzamide, tecloftalam:

boron compounds such as;

boric acid, boric acid esters, borax;

formaldehyde and formaldehyde donor compounds such as:

benzyl alcohol mono-(poly)hemiformal, 1,3-bis(hydroxymethyl)-5,5-dimethylimidazolidine-2,4diones (DM-DMH), bisoxazolidines, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis (hydroxymethyl)urea, dazomet, dimethylolurea, 4,4-dimethyloxazolidines, ethylene glycol hemiformal, 7-ethylbicyclooxazolidines, hexahydro-S-triazines, hexamethylenetetramine, N-hydroxymethyl-N'-methylthiourea, methylenebismorpholine, sodium N-(hydroxymethyl)glycinate, N-methylolchloroacetamide, oxazolidines, paraformaldehyde, tauroline, tetrahydro-1,3-oxazine, tetramethylolacetylenediurea (TMAD);

isothiazolinones such as:

N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneisothiazolinone, 4,5-benzisothiazolinone;

aldehydes such as:

cinnamaldehyde, formaldehyde, glutaraldehyde, β-bromocinnamaldehyde, o-phthalaldehyde;

thiocyanates such as:

thiocyanatomethylthiobenzothiazole, methylene bisthiocyanate;

quaternary ammonium compounds and guanidines such as:

benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, N-hexadecyltrimethylammonium chloride, 1-hexadecylpyridinium chloride, iminoctedine tris(albesilate);

phenols such as:

tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, p-hydroxybenzoic acid methyl ester, p-hydroxybenzoic acid ethyl ester, p-hydroxybenzoic acid propyl ester, p-hydroxybenzoic acid butyl ester, p-hydroxybenzoic acid octyl ester, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and alkali metal and alkaline earth metal salts thereof;

microbicides with activated halogen group such as:

bronopol, Bronidox, 2-bromo-2-nitro-1,3-propanediol, 2-bromo-4'-hydroxyacetophenone, 1-bromo-3-chloro-4,4,5,5-tetramethyl-2-imidazoldinone, β-bromo-β-nitrostyrene, chloroacetamide, chloramine T, 1,3-dibromo-4,4,5,5-tetramethyl-2-imidazoldinones, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl(2-chlorocyanovinyl)sulfone, phenyl(1,2-dichloro-2-cyanovinyl)sulfone, trichloroisocyanuric acid;

pyridines such as:

1-hydroxy-2-pyridinethione (and its Cu, Na, Fe, Mn, Zn salts), tetrachloro-4-methylsulfonylpyridine, pyrimethanol, mepanipyrim, dipyrithione, 1-hydroxy-4-methyl-6-(2,4,4-trimethylpentyl)-2(1H)-pyridine;

methoxyacrylates or the like such as:

azoxystrobin, dimoxystrobin, fluoxastrobin, kresoximmethyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene] amino]oxy]methyl]phenyl]-3H-1,2,4-triazol-3-one (CAS-No. 185336-79-2);

metal soaps such as:

salts of the metals tin, copper and zinc with higher fatty acids, resin acids, naphthenic acids and phosphoric acid such as, for example, tin, copper and zinc naphthanate, octoate, 2-ethylhexanoate, oleate, phosphate and benzoate;

metal salts such as:

salts of the metals tin, copper, zinc, and also chromates and dichromates, such as, for example, copper hydroxycarbonate, sodium dichromate, potassium dichromate, potassium chromate, copper sulfate, copper chloride, copper borate, zinc fluorosilicate, copper fluorosilicate;

oxides such as:

oxides of the metals tin, copper and zinc such as e.g. tributyltin oxide, Cu2O, CuO, ZnO;

oxidizing agents such as:

hydrogen peroxide, peracetic acid, potassium persulfate;

dithiocarbamates such as:

cufraneb, ferban, potassium N-hydroxymethyl-N'-methyldithiobarbamate, Na or K dimethyldithiocarbamate, macozeb, maneb, metam, metiram, thiram, zineb, ziram;

nitriles such as:

2,4,5,6-tetrachloroisophthalodinitrile, disodium cyanodithioimidocarbamate;

quinolines such as:

8-hydroxyquinoline and Cu salts thereof;

other fungicides and bactericides such as;

bethoxazin, 5-hydroxy-2(5H)-furanone; 4,5-benzdithiazolinone, 4,5-trimethylenedithiazolinone, N-(2-p-chlorobenzoylethyl)hexaminium chloride, 2-oxo-2-(4-hydroxyphenyl)acethydroximoyl chloride, tris-N-(cyclohexyldiazeniumdioxy)aluminum, N-(cyclohexyldiazeniumdioxy)tributyltin and K salts, iprovalicarb, fenhexamid, spiroxamin, carpropamid, diflumetorin, quinoxyfen, famoxadone, polyoxorim, acibenzolar-S-methyl, furametpyr, thifluzamide, methalaxyl-M, benthiavalicarb, metrafenon, cyflufenamid, tiadinil, tea tree oil, phenoxyethanol, Ag, Zn or Cu-containing zeolites alone or incorporated into polymeric materials.

Especially preferred are mixtures with azaconazole, bromuconazole, cyproconazole, dichlobutrazole, diniconazole, diuron, hexaconazole, metaconazole, penconazole, propiconazole, tebuconazole, dichlofluanid, tolylfluanid, fluorfolpet, methfuroxam, carboxin, benzo[b]thiophene S,S-dioxide-carboxylic acid cyclohexylamide, fenpiclonil, 4-(2,2-difluoro-1,3-benzodioxol-4-yl)-1H-pyrrole-3-carbonitrile, butenafin, imazalil, N-methylisothiazolin-3-one, 5-chloro-N-methylisothiazolin-3-one, N-octylisothiazolin-3-one, dichloro-N-octyl-isozhiazolinone, mercaptobenzthiazole, thiocyanatomethylthiobenzothiazole, thiabendazole, benzisothiazolinone, benzyl alcohol (hemi)formal, N-methyloichloroacetamide, glutaraldehyde, omadine, Zn omadine, dimethyl dicarbonate, 2-bromo-2-nitro-1,3-propanediol, bethoxazin, o-phthaldialdehyde, 2,2-dibromo-3-nitrilepropionamide, 1,2-dibromo-2,4-dicyanobutane, 1,3-bis(hydroxymethyl)-5,5-dimethylimidazolidine-2,4-diones (DMDMH), tetramethylolacetylenediurea (TMAD), ethylene glycol hemiformal, p-hydroxybenzoic acid, carbendazim, chlorophene, 3-methyl-4-chlorophenol, o-phenylphenol, Furthermore, in addition to the fungicides and bactericides stated above, highly effective mixtures are also produced with other active, ingredients:

insecticides/acaricides/nematicides:

abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,

*Bacillus thuringiensis*, barthrin, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrifluron, bromoohos A, bromophos M, bufencarb, buprofezin, butathiophos, butocarboxin, butoxycarboxim, cadusafos, carbaryl, carbofuran, carbophenothion, carbosulfan, cartap, chinomethionat, cloethocarb, chlordane, chlorethoxyfos, chlorfenapyr, chlorfenvinphos, chlorfluazuron, chlormephos, N-[(3-chloro-3-pyridinyl)-methyl]-N'-cyano-N-methyl-ethanimidamide, chlorpicrin, chlorpyrifos A, chlorpyrifos M, cis-resmethrin, clocythrin, clothiazoben, cypophenothrin, clofentezin, cournaphos, cyanophos, cycloprothrin, cyfluthrin, cyhalothrin, cyhexatin, cypermethrin, cyromazine, decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialon, diflubenzuron, dimethoate, 3,5-dimethylphenyl methyl carbamate, dimethyl(phenyl)silylmethyl 3-phenoxybenzyl ether, dimethyl (4-ethoxyphenyl)silylmethyl 3-phenoxybenzyl ether, dimethylvinohos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan, fosthiazate, fubfenprox, furathiocarb, halofenocid, HCH (CAS RN: 58-89-9), heptenophos, hexaflumuron, hexythiazox, hydramethylnon, hydroprene, imidacloprid, imiprothrin, indoxycarb, iprinomectin, iprobenfos, isazophos, isoamidophos, isofonphos, isoprocarb, isoprothiolane, isoxathion, ivermectin, kadedrin, lambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NI 125, nicotine, nitenpyram, noviflumuron, omethoate, oxamyl, oxydemethon M, oxydeprofos, parathion A, parathion M, penfluron, permethrin, 2-(4-phenoxyphenoxy)ethyl ethyl carbamate, phenthoate, phorate, phosalone, phosmet, phosphamidon, phoxim, pirimicarb, pirimiphos M, pirimiphos A, prallethrin, profenophos, promecarb, propaphos, propoxur, prothiophos, prothoate, pymetrozine, pyrachlophos, pyridaphenthion, pyresmethrin, pyrethrum, pyridaben, pyridalyl, pyrimidifen, pyriproxifen, pyrithiobac-sodium, quinalphos, resmethrin, rotenone, salithion, sebufos, silafluofen, spinosad, spirodiclofen, spiromesifen, sulfotep, sulprofos, tau-fluvalinate, tar oils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathene, triazophos, triazamate, triazuron, trichlorfon, triflumuron, trimethacarb, vamidothion, xylylcarb, zetamethrin;

molluscicides:

fentin acetate, metaldehyde, methiocarb, niclosamide;

herbicides and algicides:

acetochlor, acifluorfen, aclonifen, acrolein, alachlor, alloxydim, ametryn, amidosulfuron, amitrole, ammonium sulfamate, anilofos, asulam, atrazine, azafenidin, aziptrotryn, azimsulfuron, benazolin, benfluralin, benfuresat, bensulfuron, bensulfid, bentazon, benzofencap, benzthiazuron, bifenox, bispyribac, bispyribac-sodium, borax, bromacil, bromobutide, bromofenoxim, bromoxynil, butachror, butamifos, butralin, butylate, bialaphos, benzoyl-prop, bromobutide, butroxydim, carbetamid, carfentrazone-ethyl, carfenstrol, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuren, chlorpropham, chlorsulfuron, chlorthal, chlorthiamid, cinmethylin, cinofulsuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulfarnuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomat, 2,4-DB, desmedipham, desmetryn, dicamba, dichlobenil, dimethamid, dithiopyr, dimethametryn, eglinazin, endothal, EPTC, esprocarb, ethalfluralin, ethidimuron, ethofumesat, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, flurochloridone, fluroxypyr, fomesafen, fosamine, fosametine, flamprop-isopropyl, flamprop-isooropyl-L, flufenpyr, flumiclorac-pentyl, flumipropyn, flumioxzim, flurtamon, flumioxzim, flupyrsulfuron-methyl, fluthiacet-methyl, glyphosates, glufosinate-ammonium, haloxyfop, hexazinone, imazamethabenz, isoprofuron, isoxaben, isoxapyrifop, imazapyr, imazaquin imazethapyr, ioxynil, isopropalin, imazosulfuron, imazomox, isoxaflutole, imazapic, ketospiradox, lactofen, lenacil, linuron, MCPA, MCPA hydrazide, MCPA-thioethyl, MCPB, mecoprop, mecoprop-P, mefenacet, mefluidid, mesosulfuron, metam, metamifop, metamitron, metazachlor, methabenzthiazuron, mathazole, methoroptryne, methyldymron, methyl isothiocyanate, metobromuron, metoxuron, metribuzin, metsulfuren, molinate, monalid, monolinuron, MSMA, metolachlor, metosulam, metobenzuron, naproanilide, napropamide, naptalam, neburon, nicosulfuron, norflurazone, sodium chloride, oxadiazone, oxyfluorfen, oxysulfuron, orbencarb, oryzalin, oxadiargyl, propyzamide, prosulfocarb, pyrazolates, pyrazolsulfuron, pyrazoxyfen, pyribenzoxim, pyributicarb, pyridat, paraquat, pebulat, pendimethalin, pentachlorophenol, pentoxazon, pentanochlor, petroleum oils, phenmedipham, picloram, piperophos, pretilachlor, primisulfuron, prodiamine, profoxydim, prometryn, propachlor, propanil, propaquizafob, propazine, propham, propisochlor, pyriminobac-methyl, pelargonic acid, pyrithiobac, pyraflufen-ethyl, quinmerac, quinooloamine, quizalofop, quizalofop-P, quinchlorac, rimsulfuron, sethoxydim, sifuron, simazine, simetryn, sulfosulfuron, sulfometuron, sulfentrazone, sulcotrione, sulfosate, tar oils, TCA, TCA-sodium, tebutam, tebuthiuron, terbacil, terbumeton, terbutylazine, terbutryn, thiazafluoron, thifensulfuron, thiobencarb, thiocarbazil, tralkoxydim, triallate, triasulfuron, tribenuron, triclopyr, tridiphane, trietazine, trifluralin, tycor, thdiazimin, thiazopyr, triflusulfuron, vernolate.

Likewise encompassed by the invention is a process for preparing penflufen-containing polymer particles by performing a radical oil-in-water emulsion polymerization in which at least one ethylenically unsaturated monomer is polymerized in the presence of penflufen or its salts and acid addition compounds and in the presence of an oil-soluble radical initiator.

The penflufen-containing polymer particles of the invention are normally produced in such a way that first of all an emulsion is prepared. For the preparation of this emulsion, generally speaking, first of all the monomers and penflufen or its salts and acid addition compounds are mixed, optionally in the presence of further auxiliaries. The addition here may be made such that the complete amount of the monomers and of the penflufen is added to the aqueous solution in one step. Alternatively, the addition may be metered. In the case of the metered addition, the addition is made generally at least over a period of 0.5 h. Preferably the addition takes place within a period of 0.5 to 5 hours. Optionally a neural pH is established. The oil-in-water emulsion of monomers, penflufen and optionally low molecular weight emulsifiers, protective colloids and costabilizers is generally converted into an emulsion with particles of the desired size, with the generation of high shearing forces. In order to generate high shearing forces, it is generally the case that rotor-stator systems such as Ultraturrax, ultrasound, high-pressure dispersers, or nozzle assemblies through which flow takes place axially are used. Typically then the radical initiator is added. The radical initiator may, however, equally well have been added to the mixture of monomers and penflufen before the mixture is emulsified. In general the resulting emulsion is then heated.

The heated emulsion is typically stirred for a subsequent period of 1 to 20 hours, preferably 5 to 15 hours. The resultant suspension of the penflufen-containing polymer particles of the invention does not generally require any further working-up. The aqueous suspension of the polymer particles of the invention may therefore be used in the existing form for protecting technical materials. Alternatively, the penflufen-containing polymer particles may also be isolated and dried and then processed to penflufen-containing compositions by addition of solvents and diluents, or the aqueous suspension of the penflufen-containing polymer particles of the invention may be converted to penflufen-containing compositions by addition of thickeners, defoamers or in-container preservatives. The penflufen-containing polymer particles may be isolated, for example, by filtration and evaporation of the water, in a spray dryer, for example. If it is necessary to adjust the pH within the process of the invention for preparing the penflufen-containing polymer particles, the pH adjustment is typically accomplished using alkali metal salts of carbonates, hydrogen carbonates, phosphates, hydrogen phosphates, dihydrogen phosphates, citrates, or by using alkali metal compounds of weak organic acids.

The preparation of the penflufen-containing polymer particles in accordance with the invention is preferably accomplished in a manner which involves first introducing the aqueous solution, preferably containing low molecular weight emulsifiers. A further mixture, which comprises the monomers and the active ingredients, especially penflufen, and possibly further auxiliaries, and radical initiators is then either metered in to the aqueous solution or else added thereto substantially in one amount. Then preferably the radical initiator is added. The emulsion is thereafter preferably emulsified with high shearing forces in order to arrive at the desired particle size. The emulsion is then preferably heated and stirred for a subsequent period of preferably 8 to 15 hours. The aqueous suspension of the penflufen-containing polymer particles is preferably then processed to penflufen-containing compositions using thickeners, defoamers or in-container preservatives.

The polymerization takes place in general at temperatures between 50° C. and 90° C. The polymerization may alternatively be conducted at higher or lower temperatures. The polymerization takes place preferably at 60° C. to 80° C.

Employed in general is 0.1 wt % to 30 wt %, preferably 0.2 wt % to 20 wt % and more preferably 0.5 wt % to 15 wt % of penflufen, based on the total amount of monomers in the process of the invention for preparing the penflufen-containing polymer particles.

The molecular weights of the penflufen-containing polymer particles of the invention may vary within a very wide range, the particles preferably having a molar mass of 10 000 to 100 000 g/mol.

The penflufen-containing polymer particles of the invention customarily have an average particle diameter of less than 1.5 µm, preferably from 100 nm to 1 µm, more preferably 350 nm to 600 nm. The average particle diameter is determined by laser diffraction in accordance with ISO 13320-1.

Where the patent application refers to an oil phase, the intended meaning is the phase in which the substantially water-insoluble compounds used have undergone mutual dissolution. The oil phase generally includes the monomer or monomers, penflufen, radical, oil-soluble initiator, optionally a costabilizer, optionally further active ingredients, and optionally further auxiliaries.

The water phase generally includes one or more emulsifiers and/or protective colloids and optionally salts and radical scavengers which are intended to prevent the polymerization commencing in the water phase.

The ratio of oil phase to water phase may be varied within a wide range. In general the ratio is 10:1 to 1:10, preferably 5:1 to 1:5.

The penflufen-containing polymer particles of the invention may be converted into penflufen-containing compositions by addition of further adjuvants, such as, for example, solvents and diluents, antioxidants, radical scavengers, UV stabilizers, such as UV absorbers, and chelating agents, defoamers, and also further biocides, thickeners and in-container preservatives, or else may be used directly without further addition of these ingredients. Preference is given to adding solvents and diluents and then optionally thickeners, defoamers and in-container preservatives to the penflufen-containing polymer particles of the invention.

The penflufen-containing compositions may be produced in a known way, as for example by mixing of the penflufen-containing polymer particles with solvents and diluents or pressurized liquefied gases, optionally with accompanying use of thickeners, defoamers and in-container preservatives. The penflufen-containing compositions are preferably given by addition of thickeners, defoamers and in-container preservatives to the aqueous suspension of the penflufen-containing polymers. Suitable solvents and diluents include substantially the following: aromatics, such as xylene, toluene, or alkylnaphthalenes, chlorinated aromatics or chlorinated aliphatic hydrocarbons, such as chlorobenzenes or chloroethylenes, aliphatic hydrocarbons, such as cyclohexane or paraffins, e.g., petroleum fractions, alcohols, such as butanol or glycol and also their ethers and esters, and water.

Examples of thickeners used are polysaccharides, xanthan gum, sodium or magnesium silicates, heteropolysaccharides, alginates, carboxymethylcellulose, gum arabic, or polyacrylic acids. A preferred thickener used is xanthan gum.

In-container preservatives used are, for example and preferably, biocides, bactericides and fungicides.

As defoamers it is possible in general to use interface-active substances which are of only low solubility in the surfactant solution. Preferred defoamers are those deriving from natural fats and oils, petroleum derivatives or silicone fluids.

The penflufen-containing compositions could also be colored. Colorants used may be inorganic pigments, such as iron oxide, titanium oxide and Prussian blue, for example, and organic dyes, such as alizarin, azo and metal phthalocyanine dyes and trace nutrients, such as salts of iron, manganese, boron, copper, cobalt, molybdenum and zinc.

The penflufen-containing compositions contain in general between 0.1 and 90 percent by weight of penflufen-containing polymer particles, preferably between 2 and 75 percent by weight.

A subject of the present invention, therefore, are penflufen-containing compositions based on the penflufen-containing polymer particles of the invention, comprising at least one solvent or diluent and also, optionally, thickeners, optionally defoamers and optionally in-container preservatives, and optionally further antimicrobial substances. In materials protection, the penflufen-containing polymer particles of the invention and the penflufen-containing compositions can be used for protecting technical materials against infestation and destruction by unwanted microorganisms. Technical materials in the present context refer to inanimate materials which have been prepared for use in industry. For example, technical materials which are to be protected by penflufen against microbial alteration or destruction may be adhesives, sizes, paper and cardboard, textiles, leather, wood, coating materials and plastics articles, cooling lubricants and other materials which may be decomposed or infested by microorganisms. The materials to be protected extend to parts of production plants, such as cooling water circuits, for example, which may be affected by multiplication of microorganisms. For the purposes of the present invention, technical materials are preferably adhesives, sizes, paper and cardboard, leather, wood, coating materials, cooling lubricants and heat transfer fluids, particular preference being given to wood, wood products and wood-plastic composites.

The invention therefore also encompasses the use of the penflufen-containing polymer particles of the invention and of the penflufen-containing compositions for protecting technical materials.

Microorganisms which can bring about a degradation or a change in technical materials are for example bacteria, fungi, yeasts, algae and slime organisms. Penflufen is active preferably against fungi, more particularly mold fungi, wood-staining and wood-destroying fungi (*Basidiomycetes*), and also against same organisms and algae. It has been found, furthermore, that the penflufen-containing polymer particles and penflufen-containing compositions of the invention exhibit outstanding protection of wood against wood-destroying fungi (*Basidiomycetes*).

The invention therefore also encompasses the use of the penflufen-containing polymer particles of the invention and of the penflufen-containing compositions for protecting wood, wood products and wood-plastic composites against destruction by microorganisms.

Examples of microorganisms include those of the following genera:

*Alternaria,* such as *Alternaria tenuis,*
*Aspergillus,* such as *Aspergillus niger,*
*Chaetomium,* such as *Chaetomium globosum,*
*Coniophora,* such as *Coniophora puteana,*
*Fomitopsis,* such as *Fomitopsis palustris,*
*Gloeophyllum,* such as *Gloeophyllum trabeum,*
*Lentinus,* such as *Lentinus tigrinus,*
*Poria,* such as *Poria placenta,*
*Penicillium,* such as *Penicillium glaucum,*
*Polyporus,* such as *Polypom versicolor,*
*Aureobasidium,* such as *Aureobasidium pullulans,*
*Sclerophoma,* such as *Sclerophoma pityophila,*
*Stereum,* such as *Stereum sanguinolentum,*
*Trichoderma,* such as *Trichoderma viride,*
*Escherichia,* such as *Escherichia coli,*
*Pseudomonas,* such as *Pseudomonas aeruginosa,*
*Staphylococcus,* such as *Staphylococcus aureus.*

As wood-destroying *Basidiomycetes,* which may cause degradation or alteration of wood and wood-containing materials, mention may be made, by way of example and preference, of the following:

*Coniophora,* such as *Coniophora puteana,*
*Lentinus,* such as *Lentinus tigrinus, Antrodia,* such as *Antrodia sinuosa,*
*Polyporus,* such as *Polyporus versicolor,*
*Gloeophyllum,* such as *Gloeophylium trabeum,*
*Fomitopsis,* such as *Fomitopsis palustris,*
*Poria,* such as *Poria placenta,*
*Stereum* such as *Stereum sanguinolentum.*

Particularly preferred are the wood-destroying *Basidiomycetes*, especially *Holobasidiomycetes*, Wood-destroying *Basidiomycetes* and *Holobasidiomycetes* are fungi.

The penflufen-containing polymer particles of the invention display outstanding activity against fungi, especially against wood-destroying fungi.

The invention therefore also embraces the use of the penflufen-containing polymer particles of the invention and of the penflufen-containing compositions for protecting wood, wood products and wood-plastic composites against destruction by wood-destroying *Basidiomycetes*.

The penflufen-containing polymer particles and the penflufen-containing compositions are especially preferably active against species in the genera *Gloeophyllum, Coniophora, Coriolus, Stereum* or *Poria*. With even further preference, the penflufen-containing polymer particles are active against species in the genera *Coniphora* or *Poria*, especially against *Poria placenta* and *Coniphora puteana*. Further preferred still is the use of penflufen-containing polymer particles for protecting wood against *Poria placenta*.

The penflufen-containing polymer particles and penflufen-containing compositions of the invention can be incorporated very effectively into technical materials, especially into wood and wood products, by means of the application methods typically employed, such as vacuum, double vacuum, vacuum pressure, or pressure processes.

Wood is understood as comprising in particular: construction timber, wooden beams, railroad sleepers, bridge components, jetties, wooden vehicles, crates, pallets, containers, telephone poles, wooden fences, wood paneling, wooden windows and doors, joinery, and wood products which are used in housebuilding or in construction joinery.

In the context of the preparation process of the invention it is possible for the first time to produce stable penflufen-containing polymer particles. Moreover, the penflufen-containing polymer particles and penflufen-containing compositions of the invention have a good long-term effect in the protection of technical materials, particularly of wood, wood products and wood-plastic composites.

EXAMPLES

All reported particle sizes were carried out using a Beckmann Coulter LS 13320 particle measuring apparatus with PIDS module in accordance with ISO 13320-1.

Example 1

A solution of 2.88 g of SDS (Na dodecyl sulfate) and 0.163 g of sodium hydrogen carbonate in 300 g of water is admixed with an organic solution consisting of 91.7 g of methyl methacrylate, 4.3 g of penflufen, 3.84 g of hexadecane, 1.92 g of benzyl alcohol and 1.63 g of 2,2'-azobis(2-methylbutyronitrile) and the mixture is treated with an Ultraturrax (IKA T 25 digital, 11 000 rpm) for 30 minutes in order to produce an emulsion. The resulting emulsion is transferred to a 500 ml stainless steel beaker and ultrasonicated using an ultrasound probe with stirring and coding (ice bath) for 30 minutes (Hielscher Ultrasonics; Ultrasound processor UP200St with S26d7 sonotrode, amplitude 90%). After transfer to a 1000 ml three-neck flask, the emulsion is scrubbed with $N_2$ and heated slowly with stirring to 70° C. It is stirred at this temperature for a further 15 h. After cooling, a highly mobile, whitish blue suspension is obtained which has a penflufen content of 1.02% (HPLC).

Average particle size (measured by laser diffraction) 0.091 µm; 90% of the particles (vol %) are smaller than 0.128 µm.

Example 2

A solution of 2.88 g of SDS (Na dodecyl sulfate) and 0.163 g of sodium hydrogen carbonate in 200 g of water is admixed with an organic solution consisting of 91.7 g of methyl methacrylate, 1.92 g of divinylbenzene, 4.3 g of penflufen, 3.84 g of hexadecane and 1.63 g of 2,2-azobis (2-methylbutyronitrile) and run (in circulation) through an Ultraturrax (IKA T 25 digital, 10 800 rpm) for 15 minutes in order to produce an emulsion. After transfer to a 1000 ml three-neck flask, the emulsion is scrubbed with $N_2$ and heated slowly with stirring to 70° C. It is stirred at this temperature for a further 15 h. After cooling, a highly mobile, white suspension is obtained, containing 1.81% of penflufen (HPLC).

Average particle size (measured by laser diffraction) 0.571 µm; 90% of the particles (vol %) are smaller than 1.193 µm.

Example 3

A solution of 2.88 g of SDS (Na dodecyl sulfate) and 0.163 g of sodium hydrogen carbonate in 200 g of water is admixed with an organic solution consisting of 91.7 g of methyl methacrylate, 1.92 g of divinylbenzene, 4.3 g of penflufen, 3.84 g of hexadecane and 1.63 g of 2,2'-azobis (2-methylbutyronitrile) and run (in circulation) through an Ultraturrax (IKA T 25 digital/attachment DK 25.11; 10 800 rpm) for 15 minutes in order to produce an emulsion. After transfer to a 1000 ml three-neck flask, the emulsion is scrubbed with $N_2$ and heated slowly with stirring to 70° C. It is stirred at this temperature for a further 15 h. After cooling, a highly mobile, whitish suspension is obtained which has a penflufen content of 1.51% (HPLC).

Average particle size (measured by laser diffraction) 0.571 µm; 90% of the particles (vol %) are smaller than 1.193 µm.

Example 4

A solution of 2.88 g of SDS (Na dodecyl sulfate) and 0.163 g of sodium hydrogen carbonate in 200 g of water is admixed with an organic solution consisting of 45.85 g of methyl methacrylate. 45.85 g of n-buthyl methacrylate, 4.3 g of penflufen, 3.84 g of hexadecane and 1.63 g of 2,2'-azobis(2-methylbutyronitrile) and run (in circulation) through an Ultraturrax (IKA T 25 digital/attachment DK 25.11; 10 800 rpm) for 15 minutes in order to produce an emulsion. After transfer to a 1000 ml three-neck flask, the emulsion is scrubbed with $N_2$ and heated slowly with stirring to 70° C. It is stirred at this temperature for a further 15 h. After cooling, a highly mobile, whitish blue suspension is obtained which has a penflufen content of 1.44% (HPLC).

Average particle size (measured by laser diffraction) 0.365 µm; 90% of the particles (vol %) are smaller than 0.881 µm.

Example 5

A solution of 2.88 g of SOS (Na dodecyl sulfate) and 0.163 g of sodium hydrogen carbonate in 200 g of water is admixed with an organic solution consisting of 91.7 g of methyl methacrylate, 4.3 g of penflufen, 3.84 g of hexadecane and 1.63 g of 2,2'-azobis(2-methylbutyronitrile) and treated with an Ultraturrax (IKA T 25 digital/attachment DK 25.11; 6600 rpm) for 30 minutes in order to produce an emulsion. After transfer to a 1000 ml three-neck flask, the emulsion is scrubbed with $N_2$ and heated slowly with stirring to 70° C. It is stirred at this temperature for a further 15 h. After cooling, a highly mobile, whitish suspension is obtained which has a penflufen content of 1.48% (HPLC).

Average particle size (measured by laser diffraction) 0.574 µm; 90% of the particles (vol %) are smaller than 1.290 µm.

Example 6

A solution of 2.88 g of SDS (Na dodecyl sulfate) and 0.163 g of sodium hydrogen carbonate in 200 g of water is admixed with an organic solution consisting of 91.7 g of methyl methacrylate, 4.3 g of penflufen, 3.84 g of hexadecane and 1.63 g of 2,2'-azobis(2-methylbutyronitrile) and treated through an Ultraturrax (IKA T 25 digital/attachment DK 25.11; 14 000 rpm) for 30 minutes in order to produce an emulsion. After transfer to a 1000 ml three-neck flask, the emulsion is scrubbed with $N_2$ and heated slowly with stirring to 70° C. It is stirred at this temperature for a further 15 h. Alter cooling, a highly mobile, whitish suspension is obtained which has a penflufen content of 1.49% (HPLC).

Average particle size (measured by laser diffraction) 0.151 µm; 90% of the particles (vol %) are smaller than 0.364 µm.

Comparative Experiment 1 (With Water-Soluble Radical Initiator)

A solution of 1.15 g of SDS (Na dodecyl sulfate), 0.163 g of sodium hydrogen carbonate and 1.63 g of sodium peroxodisulfate in 144 g of water is admixed with an organic solution consisting of 87.4 g of methyl methacrylate and 8.6 g of penflufen and treated with an Ultraturrax (11 000 rpm) for 30 minutes in order to produce an emulsion. After transfer to a 1000 ml three-neck flask, the emulsion is scrubbed with $N_2$ and heated slowly with stirring to 70° C. After about 4 hours, the resulting suspension underwent thickening, and penflufen crystallized out. Visible under the microscope is a mixture of very coarse particles of agglutinated polymer and crystallized penflufen.

An experiment conducted under identical conditions with AIBN (azobis(isobutyronitrile)), an oil-soluble radical initiator, leads to a finely divided suspension without crystallization of penflufen.

What is claimed is:

1. Penflufen-containing polymer particles prepared by polymerization of at least one neutral, uncharged, ethylenically unsaturated monomer of the type M1 selected from the group consisting of styrene, divinylbenzene, esters of monoethylenically unsaturated monocarboxylic and dicarboxylic acids having 3 to 8 carbon atoms with $C_1$-$C_{20}$ alkanols or with $C_5$-$C_8$ cycloalkanols in an amount of at least 60 wt %, based on the total amount of monomers used,
in the presence of:
penflufen or its salts and acid addition compounds, and
an oil-soluble radical initiator selected from the group consisting of 2,2'-azobisisobutyronitrile, 2,2'-azobis(2-methylbutyronitrile), and mixtures thereof, in an oil-in-water emulsion polymerization.

2. The penflufen-containing polymer particles as claimed in claim 1, wherein the ethylenically unsaturated monomers are selected from the group consisting of methyl acrylate, ethyl acrylate, n-butyl acrylate, isobutyl acrylate, tert-butyl acrylate, n-hexyl acrylate, 2-ethylhexyl acrylate, 3-propylheptyl acrylate, stearyl acrylate, methyl methacrylate, ethyl methacrylate, n-butyl methacrylate, isobutyl methacrylate, tert-butyl methacrylate, n-hexyl methacrylate and stearyl methacrylate, divinylbenzene and mixtures of these monomers.

3. The penflufen-containing polymer particles as claimed in claim 1, wherein the ethylenically unsaturated monomers are composed of 80 to 99.9 wt% of monomers M1 and 0.1 wt% to 20 wt% of monomers M2, based on the total amount of monomers used, wherein the monomers M2 are selected from the group consisting of α,β-ethylenically unsaturated $C_3$-$C_8$ monocarboxylic and $C_4$-$C_8$ dicarboxylic acids, 2-(N,N,N-trimethylammonium)ethyl acrylate chloride, 2-(N,N,N-trimethylammonium)ethyl methacrylate chloride, 2-(N,N,N-trimethylammonium)ethylmethacrylamide chloride, 3-(N,N,N-trimethylammonium)propylacrylamide chloride, 3-(N,N,N-trimethylammonium)propylmethacrylamide chloride, 2-(N,N,N-trimethylammonium)ethylacrylamide chloride, and also the corresponding methosulfates and sulfates, and mixtures of these monomers.

4. The penflufen-containing polymer particles as claimed in claim 3, wherein:
an amount of penflufen or its salts and acid addition compounds is 0.5 to 15 wt%, based on the total amount of monomers used; and
an amount of initiators is 0.1 wt% to 5 wt%, based on the total amount of monomers used.

5. The penflufen-containing polymer particles as claimed in claim 4, wherein the amount of the initiators is 0.1 wt% to 3 wt%, based on the total amount of monomers.

6. The penflufen-containing polymer particles as claimed in claim 1, wherein an amount of penflufen or its salts and acid addition compounds is between 0.5 to 15 wt%, based on the total amount of monomers used.

7. The penflufen-containing polymer particles as claimed in claim 1, additionally comprising further antimicrobially active compounds selected from fungicides, bactericides, herbicides and insecticides.

8. The penflufen-containing polymer particles as claimed in claim 1, wherein the particles have a diameter of 100 nm to 1 µm.

9. A penflufen-containing composition comprising penflufen-containing polymer particles as claimed in claim 1, and at least one solvent or diluent.

10. A process for preparing the penflufen-containing polymer particles of claim 1, the process comprising polymerizing the at least one ethylenically unsaturated monomer of the type M1 in the presence of:
the penflufen or its salts and acid addition compounds, and
the oil-soluble radical initiator,
in the oil-in-water emulsion polymerization.

11. The process for preparing penflufen-containing polymer particles as claimed in claim 10, wherein the polymerization is carried out at a temperature of 50° C. to 90° C.

12. The process for preparing the penflufen-containing polymer particles as claimed in claim 10, wherein the polymerization is conducted in the presence of $C_{14}$-$C_{25}$ alkanes and $C_{14}$-$C_{25}$ cycloalkanes, and mixtures thereof.

13. A method for protecting technical materials against destruction by microorganisms, the method comprising incorporating the penflufen-containing polymer particles as claimed in claim 1 into technical materials.

14. The method as claimed in claim 13, wherein the technical material is wood, wood-plastic composites, and/or a wood product.

* * * * *